United States Patent
Kagayama et al.

[11] Patent Number: 5,817,333
[45] Date of Patent: Oct. 6, 1998

[54] LIPOSOME PREPARATION CONTAINING A TRICYCLIC COMPOUND

[75] Inventors: Akira Kagayama, Ikoma; Yuji Tokunaga, Sanda; Atsunori Kaibara, Takatsuki; Sachiyo Tanimoto, Kadoma; Takehisa Hata, Nagaokakyo, all of Japan

[73] Assignee: Fujisawa Pharmaceutical Co., Ltd., Osaka, Japan

[21] Appl. No.: 446,305

[22] Filed: May 22, 1995

Related U.S. Application Data

[63] Continuation of Ser. No. 211,834, filed as PCT/JP92/01388 Oct. 26, 1992 published as WO93/08802 May 13, 1993, abandoned.

[30] Foreign Application Priority Data

Oct. 31, 1991 [JP] Japan ................................ 3-313422

[51] Int. Cl.$^6$ .................................................. A61K 9/127
[52] U.S. Cl. .............................................. 424/450; 514/885
[58] Field of Search .............................. 424/450; 514/885

[56] References Cited

U.S. PATENT DOCUMENTS

| | | | |
|---|---|---|---|
| 4,863,740 | 9/1989 | Kissed | 424/450 |
| 4,963,362 | 10/1990 | Rahman | 424/450 |
| 4,996,193 | 2/1991 | Hewitt | 514/11 |
| 5,202,116 | 4/1993 | Byron | 424/85.1 |
| 5,260,301 | 11/1993 | Nakanishi et al. | 514/291 |

FOREIGN PATENT DOCUMENTS 0 323 042 7/1989 European Pat. Off. .

OTHER PUBLICATIONS

Mezei, Life Science 26, 1473 1980.
Poznansky. Pharmacol. Review 36 #4, 1984.

*Primary Examiner*—Gollamudi S. Kishore
*Attorney, Agent, or Firm*—Oblon, Spivak, McClelland, Maier & Neustadt, P.C.

[57] ABSTRACT

A liposome preparation containing an immunosuppresive tricylic compound or a pharmaceutically acceptable salt thereof. Since the tricyclic compound is entrapped stably and quantitatively into the liposomes, a broad variety of drug forms and pharmaceutical preparations insuring a long duration of efficacy can be provided.

3 Claims, 1 Drawing Sheet

LIPOSOME PREPARATION CONTAINING A TRICYCLIC COMPOUND

This application is a Continuation of application Ser. No. 08/211,834, filed on Apr. 29, 1994, now abandoned, which was filed as International Application No. PCT/JP92/01388, filed on Oct. 26, 1992.

FIELD OF THE INVENTION

This invention relates to a pharmaceutical liposome preparation containing a tricyclic compound or a pharmaceutically acceptable salt thereof shown by the general formula (I) presented hereinafter, which is attracting attention as a substance having a potent immunosuppresive action, as an active ingredient, and more particularly, it relates to a liposome preparation comprising said active ingredient stably entrapped in liposomes and as a consequence capable of remaining stable solution in various media such as physiological saline, glucose solution for injection, water or juices and, hence, being applicable to various methods of administration including injections such as intravenous injection, intramuscular injection, and topical injections for intraarticular and the like, topical administration such as application to skin, instillation into the eye, nasal administration, and inhalation, and further, oral administration and rectal administration etc.

PRIOR ART

A compound represented by the following general formula (I) and a pharmaceutically acceptable salt thereof has been known as a substance showing immunosupressive activity (refer to Japanese Patent Laid-Open Sho 61(1986)-148181 and European Patent Laid-Open No. 0323042), for which application uses in various medical fields have been expected, including transplantation of organs such as heart, liver, kidney, bone marrow, skin, cornea, lung, pancreas, small intestine, nerve, limb:

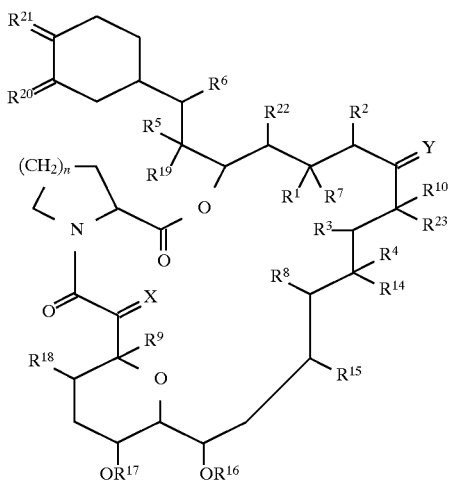

wherein each vicinal pair of $R^1$ and $R^2$, $R^3$ and $R^4$, $R^5$ and $R^6$ independently may a) represent two vicinal hydrogen atoms, or b) form a second bond between the vicinal carbon atoms to which they are attached;

in addition to the meanings above, $R^2$ may represent an alkyl group;

$R^7$ represents hydrogen, hydroxy group, protected hydroxy or alkyloxy group or, in conjunction with $R^1$, it may represent oxo group;

$R^8$ and $R^9$ independently represent hydrogen or hydroxy group;

$R^{10}$ represents hydrogen, alkyl group, alkyl group substituted by one or more hydroxyl groups, alkenyl group, alkenyl group substituted by one or more hydroxyl groups, or alkyl group substituted by oxo group;

X represents oxo group, (hydrogen atom, hydroxy group), (hydrogen atom, hydrogen atom) or —CH$_2$O—;

Y represents oxo group, (hydrogen atom, hydroxy group), (hydrogen atom, hydrogen atom) or =N—NR$^{11}$R$^{12}$ or =N—OR$^{13}$;

$R^{11}$ and $R^{12}$ independently represent hydrogen atom, or alkyl, aryl or tosyl group;

$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;

$R^{20}$ and $R^{21}$ independently represent oxo group, or they may independently represent ($R^{20}$a, hydrogen atom) and ($R^{21}$a, hydrogen atom) respectively; $R^{20}$a and $R^{21}$a independently represent hydroxy group, alkyloxy group, or OCH$_2$OCH$_2$CH$_2$OCH$_3$ or $R^{21}$a is protected hydroxy group;

in addition, $R^{20}$a and $R^{21}$a may together represent oxygen atoms in an epoxide ring;

n is 1, 2 or 3;

in addition to the meanings above, Y, $R^{10}$ and $R^{23}$, together with the carbon atoms to which they are attached, may represent a 5- or 6-membered N-, S- and/or O-containing heterocyclic ring, which may be saturated or unsaturated, and which may be substituted by one or more groups selected from alkyl group, hydroxy group, alkyl group substituted by one or more hydroxy groups, alkyloxy group, benzyl and —CH$_2$Se(C$_6$H$_5$).

Such compound (I) and its pharmaceutically acceptable salt are prepared in the same manner as the one described in the above-mentioned two patent applications. Particularly, the macrolides, which are produced by fermentation of *Streptomyces tsukubaensis* No. 9993 (FERM BP-927) or *Streptomyces hygroscopicus* subsp. *yakushimaensis* No. 7238 (FERM BP-928), are numbered FR-900506, FR-900520, FR-900523 and FR-900525.

The compound (I) and a pharmaceutically acceptable salt thereof (hereinafter the term "compound (I)" is representatively used to show them) are less water soluble and, accordingly, when they are utilized as a pharmaceutical solution, it may be considered to solubilize them by using a generally used water soluble solubilizing agent (such as ethanol, polyethylene glycol, a surfactant or the like).

However, a pharmaceutical solution prepared by the above-mentioned means may sometimes cause crystallization of the compound (I) when it is diluted with a body fluid in the applied portion, and it brings about a reduction of the bioavailability of the compound (I). In addition, several other problems remain unsolved, too, in respect of the behavior following administration to a subject, namely the degree of translocation of the drug to the tissue calling for a particularly high concentration, the adverse reactions owing to the over-necessary transfer of the drug to sites where the drug should not be distributed, and further, in respect of the duration of action and the transfer of the active substance to the target tissue after local administration.

DISCLOSURE OF INVENTION

This invention discloses a pharmaceutical liposome preparation containing the tricyclic compound (I) as an active ingredient entrapped in various forms of liposomes as a liquid preparation which is stable without undergoing precipitation on contact with the body fluid and expected to display excellent therapeutic efficacy overcoming the above problems.

BRIEF DESCRIPTION OF THE DRAWING

The drawing is a graph showing the concentration of FK506 entrapped in the liposome.

BEST MODE OF PRACTICING THE INVENTION

Figure 1:
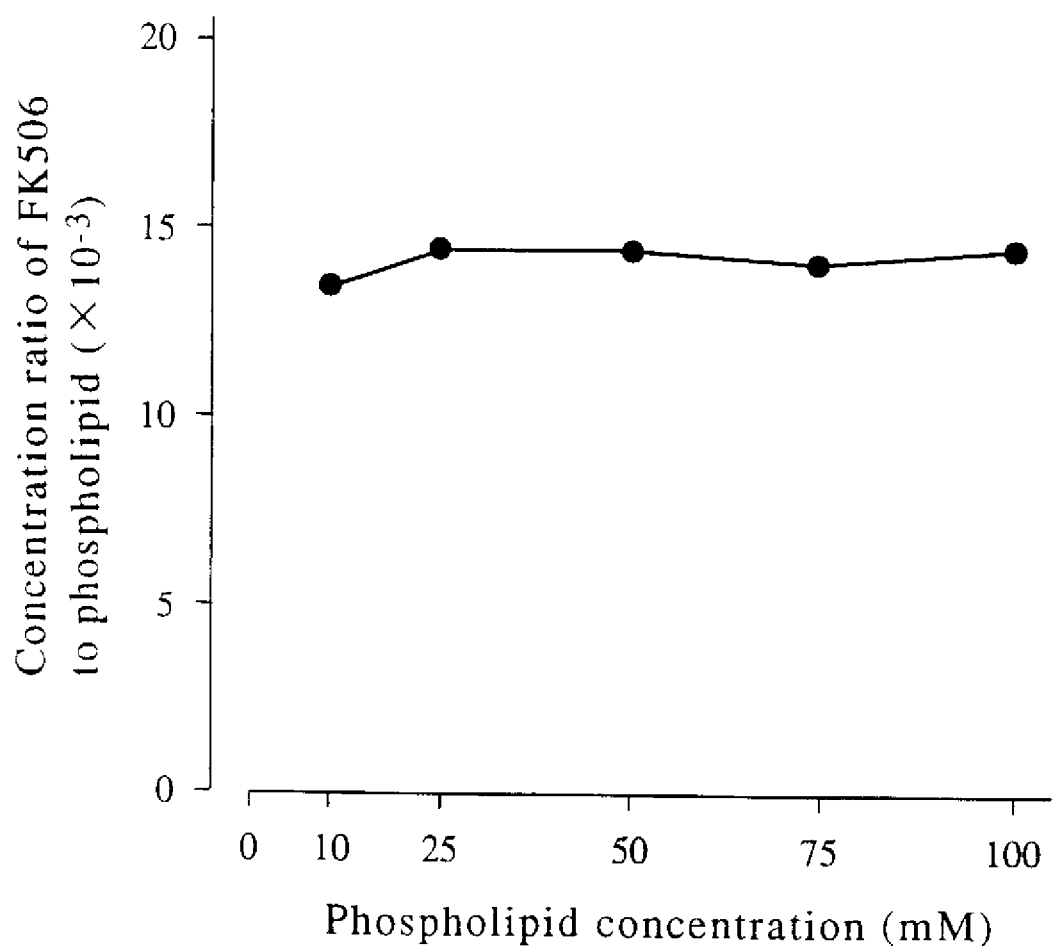

Description will be made in details to the various definitions used in the general formula (I), suitable examples and illustrations of are explained as follows.

The term "lower" as used in this specification means, unless otherwise indicated, a group having 1 to 6 carbon atoms.

Preferable examples of the "alkyl groups" are a straight or branched chain aliphatic hydrocarbon residue, for example, a lower alkyl group such as methyl, ethyl, propyl, isopropyl, butyl, isobutyl, pentyl, neopentyl, hexyl and the like.

Preferable examples of the "alkenyl groups" are a straight or branched chain aliphatic hydrocarbon residue having one double-bond, for example, lower alkenyl group such as vinyl, propenyl, butenyl, methylpropenyl, pentenyl, hexenyl and the like.

Preferable examples of the "aryl groups" include, for example, phenyl, tolyl, xylyl, cumenyl, mesityl and naphthyl and the like.

Preferable protective groups in the "protected hydroxy group" are 1-(lower alkylthio)(lower) alkyl group such as a lower alkylthiomethyl group, for example, methylthiomethyl, ethylthiomethyl, propylthiomethyl, isopropylthiomethyl, butylthiomethyl, isobutylthiomethyl and hexylthiomethyl group, more preferably, $C_1$–$C_4$ alkylthiomethyl group, most preferably, methylthiomethyl group; trisubstituted silyl group such as a tri(lower) alkylsilyl, for example, trimethylsilyl, triethylsilyl, tributylsilyl and tert-butyldimethylsilyl and tri-tert-butylsilyl, or lower alkyl-diarylsilyl, for example, methyldiphenylsilyl, ethyldiphenylsilyl, propyldiphenylsilyl and tert-butyldiphenylsilyl, more preferably tri($C_1$–$C_4$) alkylsilyl group and $C_1$–$C_4$ alkyldiphenylsilyl group, most preferably, tert-butyldimethylsilyl group and tert-butyldiphenylsilyl group; or an acyl group such as an aliphatic or aromatic acyl group derived from a carboxylic acid, sulfonic acid and carbamic acid, or an aliphatic acyl group substituted by an aromatic group.

Examples of the aliphatic acyl groups are a lower alkanoyl group optionally having one or more suitable substituents such as carboxy, for example, formyl, acetyl, propionyl, butyryl, isobutyryl, valeryl, isovaleryl, pivaloyl, hexanoyl, carboxyacetyl, carboxypropionyl, carboxybutyryl and carboxyhexanoyl; a cyclo(lower)alkoxy(lower)alkanoyl group optionally having one or more suitable substituents such as lower alkyl, for example, cyclopropyloxyacetyl, cyclobutyloxypropionyl, cycloheptyloxybutyryl, menthyloxyacetyl, menthyloxypropionyl, menthyloxybutyryl, menthyloxypentanoyl and menthyloxyhexanoyl; a camphorsulfonyl group or a lower alkylcarbamoyl group having one or more substituents such as carboxy or protected carboxy, for example, carboxy(lower)alkylcarbamoyl group, for example, carboxymethylcarbamoyl, carboxyethylcarbamoyl, carboxypropylcarbamoyl, carboxybutylcarbamoyl, carboxypentylcarbamoyl and carboxyhexylcarbamoyl, protected carboxy(lower)alkylcarbamoyl group such as tri(lower) alkylsilyl(lower)alkoxycarbonyl(lower)alkylcarbamoyl group, for example, trimethylsilylmethoxycarbonylethylcarbamoyol, trimethylsilylethoxycarbonylpropylcarbamoyl, triethylsilylethoxycarbonylpropylcarbamoyl, tertiary butyldimethylsilylethoxycarbonylpropylcarbamoyl and trimethylsilylpropoxycarbonylbutylcarbamoyl group and so on.

Examples of the aromatic acyl groups are an aroyl group optionally having one or more suitable substituents such as nitro, for example, benzoyl, toluoyl, xyloyl, naphthoyl, nitrobenzoyl, dinitrobenzoyl and nitronaphthoyl; or an arenesulfonyl group optionally having suitable substituents such as halogen, for example, benzenesulfonyl, toluenesulfonyl, xylenesulfonyl, naphthalenesulfonyl, fluorobenzenesulfonyl, chlorobenzenesulfonyl, bromobenzenesulfonyl and iodobenzenesulfonyl.

Examples of the aliphatic acyl groups substituted by aromatic group include ar(lower)alkanoyl group optionally having one or more substituents such as lower alkoxy or trihalo(lower)alkyl, for example, phenylacetyl, phenylpropionyl, phenylbutyryl, 2-trifluoromethyl-2-methoxy-2-phenylacetyl, 2-ethyl-2-trifluoromethyl-2-phenylacetyl and 2-trifluoromethyl-2-propoxy-2-phenylacetyl.

More preferable acyl groups among the aforesaid acyl groups are $C_1$–$C_4$ alkanoyl group optionally having carboxy, cyclo($C_5$–$C_6$)alkyloxy($C_1$–$C_4$)alkanoyl group having two ($C_1$–$C_4$)alkyl at the cycloalkyl group, camphorsulfonyl group, carboxy($C_1$–$C_4$)alkylcarbamoyl group, tri($C_1$–$C_4$) alkylsilyl($C_1$–$C_4$)alkoxycarbonyl($C_1$–$C_4$) alkylcarbamoyl group, benzoyl group optionally having one or two nitro groups, benzenesulfonyl group having halogen or phenyl ($C_1$–$C_4$)alkanoyl group having $C_1$–$C_4$ alkoxy and trihalo ($C_1$–$C_4$)alkyl group. Among these, the most preferable ones are, for example, acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "heterocyclic groups in the 5- or 6-membered nitrogen, sulfur and/or oxygen containing ring" include a pyrrolyl group or a tetrahydrofuryl group.

The pharmaceutically acceptable salts of the compound (I) include conventional non-toxic and pharmaceutically acceptable salts such as the salts with inorganic or organic bases, for example, an alkali metal salt such as sodium salt or potassium salt, an alkali earth metal salt such as calcium salt or magnesium salt, an ammonium salt or an amine salt such as triethylamine salt or N-benzyl-N-methylamine salt.

With regard to the compound (I) of the present invention, there may be one or more conformers or stereoisomeric pairs such as optical isomer and geometrical isomers due to the presence of asymmetric carbon atom and double bond, and such conformers or isomers are also included within a scope of the present invention.

The liposome preparation provided by this invention is now described.

The liposome preparation of this invention essentially contains the tricyclic compound (I) described above and is not subject to other conditions such as the structure and composition of liposomes, method of production of the liposomes, size thereof, the types of compounds that may be used in conjunction, etc., unless such conditions interfere with the stable entrapping of the tricyclic compound (I). Therefore, the structure of liposome may be a large unilamellar vesicle (LUV), a multilamellar vesicle (MLV) or a small unilamellar vesicle (SUV). Thus, the particle size range may be about 200–1000 nm for LUV, about 400–3500 nm for MLV and about 20–50 nm for SUV. The most preferable of them all for the stable entrapment of the tricyclic compound (I) is the MLV having a particle size of 200–1000 nm.

As the lipid constituting the liposome structure, phospholipids and nitrolipids are employed but generally phospholipids are preferred. For example, natural phospholipids such as egg yolk lecithin (phosphatidylcholine), soybean lecithin, lysolecithin, sphingomyelin, phosphatidic acid, phosphatidylserine, phosphatidylglycerol, phosphatidylinositol, phosphatidylethanolamine, diphosphatidylglycerol, cardiolipin, plasmalogen, etc., or hydrogenation products obtainable from said phospholipids by the conventional technology, and synthetic phospholipids such as dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine, eleostearoylphosphatidylserine, etc. can be mentioned.

These lipids inclusive of phospholipids can be used independently or in combination of two or more. In this constitution, lipids in which the electronegative group in the phosphatidyl group and the electropositive group in the atomic group (ethanolamine, choline and so on) bound thereto are electrically balanced so that the whole molecule is electrically neutral, for example lecithins, sphingomyelin, phosphatidylethanolamine, distearoylphosphatidylcholine, etc., are often used alone.

In contrast, (a) lipids which are electronegative as a whole, in which the atomic group (such as serine, glycerol, inositol or the like) combined to the phosphatidyl group (electronegative group) is electrically neutral, for example, phosphatidylserine, phosphatidylglycerol, phosphatidylinositol, etc. or (b) lipids such as phosphatidic acid or dicetyl phosphate, which are electronegative, can be used independently as the lipid in this invention, but it is rather recommended that they be used in combination with the neutral lipid such as those mentioned above. Among those lipids, phosphatidic acid and dicetyl phosphate do not act as the main phospholipid in the formation of liposomes but are known as liposome-forming additives and can be regarded as additives like cholesterols, stearylamine, α-tocopherol and other additives which can be used in this invention as well. As other additives which can be used, polyoxyethylene ether adduct type nonionic surfactants, gangliosides, sulfatides which have electronegative group and are acidic glycolipids, and sulfuric acid group-containing glycolipids, as liposome-forming ingredients, may be employed. These additives should be selectively added in consideration of their functions such as facilitating of the formation of liposome preparations, enhancement of the stability of liposomes in the final preparation, organ selectivity of the preparation, control of the rate of release of the active tricyclic compound (I) from the liposomes, and other factors.

There is no particular limitation on the method for preparation of liposomes but the following processes are recommended for said respective lyposome structures.

(A) Large unilamellar vesicles (LUV):
  Ether injection method [Deamer, D. W.: Ann. N. Y. Acad. Sci., 308 250(1978)]
  Surfactant method [Brunner, J., et al.: Biochim. Biophys. Acta, 455 322(1976)]
  Ditto [Kagawa, Y., et al.: J. Biol. Chem., 246 5477(1971)]
  $Ca^{2+}$ fusion method [Papahadjopoulos, D., et al.: Biochim. Biophys. Acta, 394 483(1975)]
  Freeze-thawing method [Pick, U.: Arch. Biochim. Biophys., 212 186(1981)]
  Reverse-phase evaporation method [Szoka, F., et al: Biochim. Biophys. Acta, 601 559 (1980)]
  Giant unilamellar vesicle formation [Oku, N;, et al.: Biochim. Biophys. Acta, 692 384(1982)]

(B) Multilamellar vesicles (MLV)
  Bangham method [Bangham, A. D., et al.: J. Mol. Biol., 13 238(1965)]

(C) Small unilamellar vesicles (SUV)
  Ultrasonic treatment method [Huang, C.: Biochemistry, 8 344 (1969)]
  Ethanol injection method [Kremer, J. M. H., et al.: Biochemistry, 16 3932(1977)]
  French press method [Barenholz, Y., et al.: FEBS Lett., 99 210(1979)]

All of the above processes are basic technologies for the formation of liposome vesicle and these processes can of course be used in combinations, respectively proved or modified. For example, the film strength of vesicle may be enhanced by irradiating the formed liposomes to active electromagnetic radiation such as ultraviolet light or radiation so as to induce polymerization.

The representative process for forming liposomes which is used in this invention is now described. For example, the liposome-forming material described above is dissolved in an organic solvent, such as chloroform or ethanol, together with the active ingredient, cholesterol, etc. Then, in an appropriate vessel, the solvent is distilled off under reduced pressure to form a liposome film on the inner surface of the vessel. To the vessel is added a buffer solution and the mixture is stirred to give a suspension. From this suspension, the liposomes are isolated by the conventional procedure such as filtration or centrifugation. The liposomes thus obtained are suspended in a suitable solvent, or once lyophilized and resuspended in a suitable solvent for use in therapy.

The amount of the tricyclic compound (I) in the resulting tricyclic compound (I)-containing liposome preparation is preferably set according to the application site. The recommended concentration is 0.05–50 mg/ml for intravenous injection, 1–50 mg/ml for intramuscular injection, 0.1–50 mg/ml for instillation into the eye and 0.1–50 mg/ml for oral administration. According to such sites of administration, the composition can be diluted with aqueous media such as water, physiological saline, glucose solution for injection, juice, milk and so on. Of course, the concentrations mentioned above are lowered by such dilution.

The tricyclic compound-containing liposome pharmaceutical preparation at this invention can also be obtained when the compounds disclosed in the documents listed below are employed as active ingredients, such as EP-A-353678, Japanese Patent Application No. HEI 2(1990)-74330, PCT/GB90/01262, EP-A-413532, PCT/JP91/00314, British Patent Application No. 9012963.6, British Patent Application No. 9014136.7, British Application No. 9014681.2, British Patent Application No. 9014880.0, British Patent Application No. 9014881.8, British Patent Application No. 9015098.8, British Patent Application No. 9016115.9, British Patent Application No. 9016693.5, EP-A-323865, EP-A-349061, EP-A-358508, EP-A-364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576.A, EP-A-402931 and EP-A-427680.

The liposome preparation containing the tricyclic compound (I), provided by this invention, as apparent from the test result shown in FIG. 1, is almost quantitatively entrapped in the liposome. In the test relevant to FIG. 1, FK506 described hereinafter was used as the tricyclic compound (I). Thus, FIG. 1 shows the relation between the concentration of the phospholipid formed in said solvent such as chloroform or ethanol (abcissa) and the concentration of FK506 entrapped in the formed liposomes (ordinate). It can be understood from the constant FK506 concentration that the contents control in the preparating process is done with remarkably high accuracy. As seen from the data presented in FIG. 1, the molar ratio of phospholipid to FK506 is about 1000:15 and it is recommendable that the preparation of liposomes should be carried out using this value as a reference.

EXAMPLE 1

As the compound (I), the following compound in which:
$R^1$, $R^2$, $R^8$, $R^{23}$=hydrogen
$R^7$, $R^9$=hydroxyl group
$R^{10}$=allyl group
$R^{14}$, $R^{15}$, $R^{16}$, $R^{17}$, $R^{18}$, $R^{19}$, $R^{22}$=methyl group
$R^{20}$=($R^{20}$a, H) ($R^{20}$a =methoxy)
$R^{21}$=($R^{21}$a, H) ($R^{21}$a =hydroxyl group)
X, Y=oxo group n=2
$R^3$, $R^4$=form a second bond between the vicinal carbon atoms to which they are attached
$R^5$, $R^6$=form a second bond between the vicinal carbon atoms to which they are attached, being in a free form was used. The compound has an excellent immunosupressive activity and is referred to hereinafter as FK506.

In a suitable amount of chloroform-methanol (4/1, v/v) were dissolved egg yolk phosphatidylcholine (3.05 g), cholesterol (1.16 g), phosphatidylserine (0.762 g) and FK506 (82.2 mg) and the solution was concentrated to dryness under reduced pressure to form a thin film on the inner wall of the vessel. To the vessel was added 50 ml of phosphate-buffered physiological saline and the system was stirred using a vortex mixer (manufactured by Iuchi Seieido). The resultant suspension was divided into 10 ml and 40 ml.

(1) The suspension, 10 ml, was serially filtered through polycarbonate membranes of 3 μm and 1 μm in pore size respectively to provide a liposome preparation. This liposome preparation was diluted with phosphate-buffered physiological saline so that its FK506 content was 0.5 mg/ml. The mean diameter of liposomes was 432 nm.

(2) The suspension, 40 ml, was treated with a nanomizer (manufactured by Cosmo Instrumentation Co.) at 4° C. under 7 atm. for 10 minutes and, then, centrifuged at 4° C., at 15000 rpm for 60 minutes. The FK506 content of the resultant supernatant liquid was diluted with phosphate-buffered physiological saline to a concentration of 0.5 mg/ml. The mean particle diameter of the liposomes was not greater than 30 nm.

EXAMPLE 2

In a suitable amount of chloroform-methanol (4/1, v/v) were dissolved egg yolk phosphatidylcholine (7.62 g), cholesterol (2.32 g) and FK506 (164.4 mg) and the solution was concentrated to dryness under reduced pressure to form a thin film on the inner wall of the vessel. To this vessel was added 100 ml of phosphate-buffered physiological saline and the system was stirred using a vortex mixer (manufactured by Iuchi Seieido) to provide a suspension.

(1) The suspension, 10 ml, was serially filtered through polycarbonate membranes, 3 μm and 1 μm in pore size respectively to provide a liposome preparation. This liposome preparation was diluted with phosphate-buffered physiological saline so that its FK506 content was 0.5 mg/ml. The mean diameter of liposomes was 587 nm.

(2) The suspension, 40 ml, was treated with a nanomizer (manufactured by Cosmo Instrumentation Co.) at 4° C. under 7 atm. for 30 minutes and, then, centrifuged at 4° C., at 15000 rpm for 60 minutes. The FK506 content of the resultant supernatant liquid was diluted with phosphate-buffered physiological saline to a concentration of 0.5 mg/ml. The mean particle diameter of the liposomes was not greater than 30 nm.

EXAMPLE 3

In a suitable amount of chloroform-methanol (4/1, v/v) were dissolved egg yolk phosphatidylcholine (3.81 g) and cholesterol (1.16 g) and the solution was concentrated to dryness under reduced pressure to form a thin film on the inner wall of the vessel. To this vessel was added 50 ml of phosphate-buffered physiological saline and the system was stirred using a vortex mixer (manufactured by Iuchi Seieido) to provide a suspension.

This suspension, 50 ml, was treated with a nanomizer (Cosmo Instrumentation Co.,) at 4° C. under 7 atm. for 15 minutes and, then, centrifuged at 4° C., at 15000 rpm for 60 minutes. The resultant supernatant liquid was filtered through Millex GV (pore size 0.22 μm, manufactured by Millipore) to provide a suspension of liposomes. This liposome suspension was diluted with phosphate-buffered physiological saline to provide liposome suspensions of various phospholipid concentrations. To 10 ml of each liposome suspension was added about 20 mg of the bulk powder of FK506 and the mixture was allowed to stand under stirring at room temperature. Test samples were collected at regular time intervals after addition of the bulk powder and each sample was centrifuged at 10000 rpm for 1 minute and the supernatant liquid was filtered through Millex GV. The FK506 concentration of the filtrate was measured by high performance liquid chromatograhy and the amount of FK506 entrapped in the liposomes was calculated. The results after a definite time are shown in FIG. 1.

Industrial Field of Utilization

Having the above-described structure, the liposome prepartion of this invention allows the hardly water-soluble tricyclic compound (I) to be provided in the form of a stable solution which does not cause crystallization of the active ingredient on contact with the body fluid and, hence, shows high bioavailability and stability. Therefore, it can assume a broad variety of pharmaceutical drug forms such as injections, eye-drops, nasal drops, inhalants, transdermic drug, local injections, etc. Moreover, it is possible to enhance the delivery of tricyclic compound (I) to a target where a high concentration of the compound is required, or to suppress the delivery of the compound to sites where the drug is not necessarily required. As a result, practically excellent results such as potentiation of drug efficacy, alleviation of adverse reactions and extended duration of efficacy can be obtained.

The pharmaceutical formulation according to the present invention, due to the pharmacological activities, such as immunosuppressive activity and antimicrobial activity, of the tricyclo compound (I), is useful for the treatment and prevention of immune-mediated diseases such as rejection in transplantation of organs or tissue such as heart, kidney, liver, bone marrow, skin, cornea, lung, pancreas, small intestine, limb, muscle, nerve, intervertebral disk, trachea, etc.; graft-versus-host reaction to bone marrow transplantation; autoimmune diseases such as rheumatoid arthritis, systemic lupus erythematosus, Hashimoto's thyroiditis, multiple sclerosis, myasthenia gravis, type I diabetes, and the like; and further infectious diseases caused by pathogenic microorganisms.

Further, the tricyclo compounds (I) are also useful for the treatment and the prophylaxis of inflammatory and hyperproliferative skin diseases and cutaneous manifestations of immunologically-mediated illnesses, such as psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitides, erythemas, cutaneous eosinophilias, lupus erythematosus, acne and alopecia areata; various eye diseases such as autoimmune diseases and so on (e.g. keratoconjunctivitis, vernal conjunctivitis, uveitis associated with Behcet's disease, keratitis, herpetic keratitis, conical keratitis, dystrophia epithelialis corneae, corneal leukoma, ocular pemphigus, Mooren's ulcer, scleritis, Graves' ophthalmopathy, Vogt-Koyanagi-Harada syndrome, sarcoidosis, etc.); reversible obstructive airways disease, which includes conditions such as asthma (e.g. bronchial asthma, allergic asthma, intrinsic asthma, extrinsic asthma and dust asthma), particularly chronic or inveterate asthma (e.g. late asthma and airway hyper-responsiveness), bronchitis and the like; inflammation of mucosa and blood vessels such as gastric ulcers, vascular injury caused by ischemic diseases and thrombosis, ischemic bowel disease, enteritis, necrotizing enterocolitis, intestinal lesions associated with thermal burns, leukotriene $B_4$-mediated diseases; intestinal inflammations/allergies such as coeliac disease, proctitis, eosinophilic gastroenteritis, mastocytosis, Crohn's disease and ulcerative colitis; food related allergic diseases which have symptomatic manifestation remote from the gastro-intestinal tract, for example migraine, rhinitis and eczema; renal diseases such as interstitial nephritis, Goodpasture's syndrome, hemolytic-uremic syndrome and diabetic nephropathy; nervous diseases such as multiple myositis, Guillain-Barre syndrome, Meniere's disease and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, pulmonary fibrosis and idiopathic interstitial pneumonia; skin diseases such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjögren's syndrome; adiposis; eosinophilic fasciitis; periodontal disease such as lesion of gingiva, periodontium, alveolar bone, substantia ossea dentis; nephrotic syndrome such as glomerulonephritis; male pattern alopecia or alopecia senilis; muscular dystrophy; pyoderma and Sezary's syndrome; Addison disease; active oxygen-mediated diseases, for example, organ injury such as ischemia-reperfusion injury of organs (e.g. heart, liver, kidney, digestive tract) which occurs on preservation, transplantation or ischemic diseases (e.g. thrombosis, cardiac infarction): intestinal diseases such as endotoxin-shock, pseudomembranous colitis, colitis caused by drug or radiation: renal diseases such as ischemic acute renal insufficiency, chronic renal insufficiency: pulmonary diseases such as toxicosis caused by lung-oxygen or drug (e.g. paracort, bleomycins), lung cancer, pulmonary emphysema: ocular diseases such as cataracta, siderosis, retinitis, pigmentosa, senile macular degeneration, vitreous scarring, corneal alkali burn: dermatitis such as erythema multiforme, linear IgA bullous dermatitis, cement dermatitis: and others such as gingivitis, periodontitis, sepsis, pancreatitis, diseases caused by environmental pollution (e.g. air pollution), aging, carcinogens, metastasis of carcinoma, hypobaropathy; diseases caused by histamine or leukotrience $C_4$ release; and so on.

And further, the tricyclo compounds (I) have liver regenerating activity and/or activities of stimulating hypertrophy and hyperplasia of hepatocytes. Therefore, they are useful for the treatment and prevention of hepatic diseases such as immunogenic diseases (e.g. chronic autoimmune liver diseases such as the group consisting of autoimmune hepatic disease, primary biliary cirrhosis and sclerosing cholangitis), partial liver resection, acute liver necrosis (e.g. necrosis caused by toxins, viral hepatitis, shock or anoxia), hepatitis B, hepatitis non-A/non-B, cirrhosis and hepatic failure such as fulminant hepatitis, late-onset hepatitis and "acute-on-chronic" liver failure (acute liver failure on chronic liver diseases).

And further, the tricyclo compounds (I) are useful for various diseases because of their useful pharmacological activity such as augmenting activity of chemotherapeutic effect, preventing or treating activity of cytomegalovirus infection, anti-inflammatory activity, and so on.

What is claimed is:

1. A preparation comprising FK506 stably entrapped in a liposome, said liposome consists essentially of phosphatidyl choline and cholesterol.

2. The liposome preparation as defined in claim 1, wherein the weight ratio of phosphatidyl choline, FK506 and cholesterol is about 46:1:14.

3. The liposome preparation as defined in claim 1, wherein the molar ratio of phosphatidyl choline to FK506 is about 1000:15.

* * * * *